United States Patent
Chen

(10) Patent No.: US 12,220,425 B2
(45) Date of Patent: *Feb. 11, 2025

(54) GASTROESOPHAGEAL REFLUX DISEASE WITH FIBERS FORMED OF β-1-4-GLUCAN

(71) Applicant: Chao-Cheng Chen, Taipei (TW)

(72) Inventor: Chao-Cheng Chen, Taipei (TW)

(73) Assignee: Chao-Cheng Chen, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/455,033

(22) Filed: Nov. 16, 2021

(65) Prior Publication Data
US 2023/0015410 A1    Jan. 19, 2023

(30) Foreign Application Priority Data
Jul. 16, 2021 (TW) ................................ 110126271

(51) Int. Cl.
| | | |
|---|---|---|
| *A61K 31/716* | (2006.01) | |
| *A61K 9/70* | (2006.01) | |
| *A61K 35/74* | (2015.01) | |
| *A61P 1/04* | (2006.01) | |

(52) U.S. Cl.
CPC .............. *A61K 31/716* (2013.01); *A61K 9/70* (2013.01); *A61K 35/74* (2013.01); *A61P 1/04* (2018.01)

(58) Field of Classification Search
None
See application file for complete search history.

(56) References Cited

U.S. PATENT DOCUMENTS

2009/0252792 A1* 10/2009 Verbruggen ......... A61K 31/718
514/54

FOREIGN PATENT DOCUMENTS

WO    WO 2010/031154    *    3/2010    ............... D01F 1/00

OTHER PUBLICATIONS

Newberry et al (J Thorac Dis 11(Suppl 12):S1594-S1601, 2019) (Year: 2019).*
Azeredo et al (Frontiers in Sustainable Food Systems, 3(7), 14 pages, 2019) (Year: 2019).*
Choi et al (Nanomaterials 10:406, 24 pages, Feb. 25, 2020) (Year: 2020).*
Fass et al (J Clin Gastroenterol 41:131-137, 2007) (Year: 2007).*
Tosti et al (J Gerontol A Biol Sci Med Sci 73:318-326, 2018) (Year: 2018).*
Jones et al (Arch Otolaryngol Head Neck Surg 116:1031, 1990) (Year: 1990).*

* cited by examiner

*Primary Examiner* — Craig D Ricci
(74) *Attorney, Agent, or Firm* — Osha Bergman Watanabe & Burton LLP

(57) ABSTRACT

Provided is a method of preventing or treating gastroesophageal reflux disease, including administering to an subject in need thereof a composition including a plurality of fibers formed of β-1-4-glucan, wherein the fibers have a diameter between 15 nm and 35 nm and a mean length of between 1.5 μm and 3.5 μm.

11 Claims, No Drawings

GASTROESOPHAGEAL REFLUX DISEASE WITH FIBERS FORMED OF β-1-4-GLUCAN

1. TECHNICAL FIELD

The present disclosure relates to compositions for preventing or treating gastroesophageal reflux disease, particularly to methods for preventing or treating gastroesophageal reflux disease by administering fibers formed of β-1-4-glucan.

2. DESCRIPTION OF RELATED ART

Gastroesophageal reflux disease (GERD), as indicated by its name, refers to a disease involving reflux of gastrointestinal contents back into the esophagus, causing discomfort in the stomach, esophagus, even throat and respiratory tract, and also esophageal mucosal damage. GERD is associated mainly with a loose lower esophageal sphincter (cardia). Other factors such as esophageal emptying, peristalsis disorder, poor esophageal mucosal protection mechanism, delayed gastric emptying, diaphragmatic hernia and increased gastric pressure may also cause reflux. Gastroesophageal reflux is a chronic and recurring disease having symptoms such as heartburn, hoarseness or sore throat, dysphagia, hiccups, nausea, dry cough, and flatulence. The comorbidities of gastroesophageal reflux disease include esophagitis (such as inflammation, erosion, ulcers, bleeding, fibrosis, stricture, etc. of esophagus) and Barrett's esophagus (BE). Clinically, an upper gastrointestinal endoscopy is used, and the severity of erosive esophagitis (EE) caused by gastroesophageal reflux can be divided into four grades according to the Los Angeles classification: grade A, one (or more) mucosal break no longer than 5 mm that does not extend between the tops of two mucosal folds; grade B, one (or more) mucosal break more than 5 mm long that does not extend between the tops of two mucosal folds; grade C, one (or more) mucosal break that is continuous between the tops of two or more mucosal folds but which involve less than 75% of the circumference; and grade D, one (or more) mucosal break which involves at least 75% of the esophageal circumference.

Clinical medications for gastroesophageal reflux disease include antacids that neutralize gastric acid, protective stomach medication, and medication promoting gastrointestinal peristalsis. Among them, antacids are the drugs commonly used in treatments; however, antacids should not be taken in excessive amounts and for a long-term use, otherwise they will lead to over-inhibition of gastric acid that causes the subsequent rebound of gastric acid secretion. Also, over-inhibition of gastric acid tends to cause indigestion of food and produce a feeling of bloating. Antacids also have side effects, such as diarrhea caused by magnesium salts and constipation caused by aluminum salts. Moreover, long-term use of antacids may also affect the cardiovascular system and kidney function and increase the risk of infection. Hydrogen ion pump inhibitors are the main drugs for the treatment of gastroesophageal reflux disease, but 6% to 15% of patients with erosive esophagitis do not respond to treatment, 20% of patients with Barrett's esophagus do not respond to treatment, and 40% to 50% of patients with non-erosive reflux disease (only reflux symptoms but no mucosal inflammation and damage under gastroscopy) do not respond to treatment. Therefore, the use of hydrogen ion pump inhibitor is restricted. On the other hand, long-term use of hydrogen ion pump inhibitors is found with complications such as fractures and community acquired pneumonia and nosocomial *Clostridium difficile* associated diarrhea. Furthermore, use of hydrogen ion pump inhibitors can also affect the absorption of vitamin C and B12, and exist risk of side effects.

SUMMARY

The present disclosure provides a use of a plurality of fibers made from β-1-4-glucan for manufacture of a composition for prevention or treatment of gastroesophageal reflux disease, wherein the fibers have a diameter of between 15 nm and 35 nm and a mean length of between 1.5 μm and 3.5 μm.

In at least one embodiment of the present disclosure, the gastroesophageal reflux disease is grade A and grade B erosive esophagitis graded by Los Angeles classification.

In at least one embodiment of the present disclosure, the fibers have a length-to-diameter ratio of from 60 to 150.

In at least one embodiment of the present disclosure, the composition may be administered to an subject in a form comprising the plurality of fibers formed of β-1-4-glucan and a liquid medium, or the composition may be administered to the subject as a freeze-dried tablet.

In at least one embodiment of the present disclosure, the composition is administered at an effective amount for 1 to 4 times a day to the subject in need of prevention or treatment of gastroesophageal reflux disease, and the composition for each administration is a freeze-dried tablet including 0.02 g to 0.12 g of the plurality of fibers.

In at least one embodiment of the present disclosure, the liquid medium is water.

In at least one embodiment of the present disclosure, the fibers are in an amount of from 0.2% by weight to 1.2% by weight based on a total weight of the above-mentioned composition.

In at least one embodiment of the present disclosure, the composition comprises 0.1 mL of water with $OD_{620}$ between 0.25 and 1.25, such as between 0.4 and 1.22.

In at least one embodiment of the present disclosure, the fibers are formed by fermentation by at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*.

In at least one embodiment of the present disclosure, the bacterium is at least one selected from the group consisting of *Acetobacter xylinum, Gluconacetobacter hansenii, Gluconacetobacter xylinus,* and *Gluconacetobacter sacchari*.

In at least one embodiment of the present disclosure, the composition further includes at least one selected from the group consisting of an organic nutrient, a probiotic, a drug, a dietary fiber, a flavoring agent, a dispersing agent, a wetting agent, a lubricant, a thickening agent, a stabilizer, a preservative, an antioxidant, an antibacterial agent and a coloring agent.

In at least one embodiment of the present disclosure, the composition is administered orally to the subject in need thereof.

The present disclosure also provides a method of prevention or treatment of gastroesophageal reflux disease, comprising administering to a subject in need thereof a plurality of fibers formed of β-1-4-glucan, wherein the fibers have a diameter of from 15 nm to 35 nm and a mean length of between 1.5 μm and 3.5 μm.

The present disclosure further provides a freeze-dried tablet comprising a plurality of fibers formed of β-1-4-glucan for prevention or treatment of gastroesophageal reflux disease, wherein the fibers have a diameter of between 15 nm and 35 nm and a length of between 1.5 μm and 3.5 μm.

In at least one embodiment of the disclosed method, composition and freeze-dried tablet, the gastroesophageal reflux disease is grade A and grade B erosive esophagitis graded by Los Angeles classification.

In at least one embodiment of the disclosed method, composition and freeze-dried tablet, the fibers have a length-to-diameter ratio between 60 and 150.

In at least one embodiment of the disclosed method, composition and freeze-dried tablet, the fibers are administered 1 to 4 times a day to the subject in need of prevention or treatment of gastroesophageal reflux disease, and each administration or dose includes 0.02 g to 0.12 g of the plurality of fibers.

In at least one embodiment of the disclosed method, composition and freeze-dried tablet, the fibers are comprised in a composition and administered to the subject in need of prevention or treatment of gastroesophageal reflux disease.

In at least one embodiment of the disclosed method, composition and freeze-dried tablet, the composition is administered to the subject in a form of a freeze-dried tablet.

In at least one embodiment of the disclosed method, composition and freeze-dried tablet, the composition is administered in a form comprising the plurality of fibers formed of β-1-4-glucan and a liquid medium.

In at least one embodiment of the disclosed method, composition and freeze-dried tablet, the liquid medium is water.

In at least one embodiment of the disclosed method, composition and freeze-dried tablet, the fibers are in an amount of from 0.2% by weight to 1.2% by weight based on a total weight of the composition.

In at least one embodiment of the disclosed method, composition and freeze-dried tablet, the composition comprises 0.1 mL of water with $OD_{620}$ between 0.25 and 1.25, such as between 0.4 and 1.22.

In at least one embodiment of the disclosed method, composition and freeze-dried tablet, the fibers are formed by fermentation of at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*.

In at least one embodiment of the disclosed method, composition and freeze-dried tablet, the bacterium is at least one selected from the group consisting of *Acetobacter xylinum, Gluconacetobacter hansenii, Gluconacetobacter xylinus* and *Gluconacetobacter sacchari*.

In at least one embodiment of the disclosed method, composition, and freeze-dried tablet, the composition further comprises at least one selected from the group consisting of an organic nutrient, a probiotic, a drug, a dietary fiber, a flavoring agent, a dispersing agent, a wetting agent, a lubricant, a thickener, a stabilizer, a preservative, an antioxidant, an antibacterial agent and a coloring agent.

In at least one embodiment of the disclosed method, composition and freeze-dried tablet, the fibers are orally administered to the subject in need thereof.

The present disclosure effectively treats, improves, relieves, or prevents discomfort caused by gastroesophageal reflux using fibers formed of β-1-4-glucan, and excellent effects with almost no side effects were observed.

DETAILED DESCRIPTION

The present disclosure is illustrated by the exemplary embodiments in the following. A person skilled in the art can easily conceive the other advantages and effects of the present disclosure, based on the disclosure of the specification. However, embodiments described in the specification are not intended to limit the scope of the present disclosure. The technical features or examples listed can be combined with each other. The present disclosure can also be carried out or applied in other different implementations. It is possible to modify or alter the disclosed examples for carrying out this disclosure without contravening its scope, for different aspects and applications.

As described herein, when "including," "comprising" or "having" specific elements is recited, unless otherwise specified, it may further include other elements such as components, structures, areas, parts, devices, systems, steps, or connecting relations, rather than excluding other elements.

As used herein, the singular forms "a," "an," and "the" include plural referents unless expressly and unequivocally limited to one referent. The term "or" is used interchangeably with the term "and/of" unless the context clearly indicates otherwise.

The numerical ranges described herein are inclusive and combinable. Any value falling within the numerical range described herein can be used as the maximum or minimum value to derive the secondary range; for example, "a diameter of between 15 nm to 35 nm" should be construed to include any sub-range between the minimum value of 15 nm and the maximum value of 35 nm, e.g., 15 nm to 30 nm, 16 nm to 35 nm, and 22 nm to 28 nm; in addition, if a value falls within each range described herein (such as between the maximum value and the minimum value), it shall be deemed to be included in the scope of this disclosure.

In at least one embodiment of the present disclosure, the plurality of fibers formed of β-1-4-glucan has a diameter of 15 nm to 35 nm, for example, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm or about 35 nm. In some embodiments, the fibers of the present disclosure have a length of 1.5 μm to 3.5 μm, such as about 1.5 μm, about 1.6 μm, about 1.7 μm, about 1.8 μm, about 1.9 μm, about 2.0 μm, about 2.1 μm, about 2.2 μm, about 2.3 μm, about 2.4 μm, about 2.5 μm, about 2.6 μm, about 2.7 μm, about 2.8 μm, about 2.9 μm, about 3.0 μm, about 3.1 μm, about 3.2 μm, about 3.3 μm, about 3.4 μm or about 3.5 μm. In some embodiments of the present disclosure, the diameter of the plurality of fibers is between 15 nm and 35 nm, and the average length of the plurality of fibers is between 1.5 μm and 3.5 μm. In at least one embodiment of the present disclosure, the diameter of each of the plurality of fibers is between 15 nm and 35 nm.

The plurality of fibers formed of β-1-4-glucan in the present disclosure can be used for manufacture of a composition for prevention or treatment of gastroesophageal reflux disease, and can also be used for prevention or treatment of gastroesophageal reflux disease, comprising administering the plurality of fibers formed of β-1-4-glucan to the subject in need thereof. In some embodiments, the composition of the present disclosure may be a pharmaceutical composition, and is not limited thereto. In some embodiments of the present disclosure, the gastroesophageal reflux disease may be grade A and grade B erosive esophagitis graded by Los Angeles classification. The gastroesophageal reflux disease may refer to grade A to D erosive esophagitis according to the Los Angeles classification, or a gastroesophageal reflux diagnosed by a physician with an esophagogastroduodenoscopy (gastroscope), a 24-hour esophageal pH test, an esophageal impedance pH study, a lower esophageal sphincter pressure test, a barium swallow radiograph, a proton pump inhibitor test, consultation and patient self-assessment questionnaire. Grade A and grade B erosive esophagitis by the Los Angeles classification are usually regarded as mild gastroesophageal reflux disease. The disclosed composition effectively prevents or treats mild gastroesophageal reflux and stops or reduces medication in patients under treatment, or the patients may switch to medication with less potency. Severe gastroesophageal reflux disease, such as grade C and grade D erosive esophagitis of the Los Angeles classification, can also be treated with the composition of the present disclosure as adjunct therapy with other medication, endoscopy surgery, surgery, and other therapy and treatments.

In at least one embodiment, the plurality of fibers formed of β-1-4-glucan or the composition thereof in the present disclosure is in the form of a freeze-dried tablet, including a dosage form resulted from a freeze-drying process, such as in the form of a dry tablet. In some embodiments of the present disclosure, it can be processed by at least one of low-temperature freezing, air extraction under low temperature and low pressure, and desorption, so as to improve the overall stability of the product, and thus the product does not deteriorate easily. The excellent rehydration of the plurality of fibers thus prepared allows fast administration to the subject. In some embodiments of the present disclosure, the dosage form can be prepared through the sequential steps of low-temperature freezing, air extraction at low temperature and low pressure, and desorption. However, it should be understood that the sequence of the preparation steps is not limited thereto, and can be adjusted according to the desired features of the plurality of fibers. In some embodiments of the present disclosure, the plurality of fibers or its composition formed of β-1-4-glucan does not comprise a liquid medium, but in a form of dry powder prepared by, for example, a freeze-drying process.

In at least one embodiment of the present disclosure, the subject in need of prevention or treatment of gastroesophageal reflux disease may directly take the plurality of fibers formed of β-1-4-glucan or the composition comprising the plurality of fibers orally in a form of, for example, oral freeze-dried tablets or dry powder, with no limitation. In some embodiments of the present disclosure, the plurality of fibers may be disintegrated in saliva in mouth and enter the gastrointestinal tract by swallowing.

In at least one embodiment of the present disclosure, when the freeze-dried or lyophilized tablet or dry powder is administered to the subject in need of prevention or treatment of gastroesophageal reflux disease, the freeze-dried or lyophilized tablet or dry powder may be optionally mixed with a liquid medium first to form a composition comprising the liquid medium and the plurality of fibers. In some embodiments, the subject's cough is avoided when the composition of the present disclosure comprising a liquid medium is taken orally, since the composition in a liquid state has good fluidity and is convenient for the subject to drink. In some embodiments of the present disclosure, the liquid medium may include edible liquids, such as water, juice, tea, etc., but is not limited thereto. In some embodiments of the present disclosure, since the prepared composition includes a liquid medium, the subject does not need to mix the plurality of fibers prepared by the present disclosure with a liquid medium before taking the composition of the present disclosure.

In at least one embodiment of the present disclosure, based on the total weight of the composition, the amount of the plurality of fibers may be between 0.2% by weight and 1.2% by weight, so as to increase its dispersion rate. For example, the amount of fibers may be about 0.2% by weight, about 0.3% by weight, about 0.4% by weight, about 0.5% by weight, about 0.6% by weight, about 0.7% by weight, about 0.8% by weight, about 0.9% by weight, about 1.0% by weight, about 1.1% by weight, or about 1.2% by weight. In some embodiments of the present disclosure, when the amount of the plurality of fibers is less than 0.2% by weight, the plurality of fibers may not provide enough hydroxyl groups, thereby affecting the interfacial tension of the liquid medium to some extent. In some embodiments of the present disclosure, when the amount of the plurality of fibers is less than 0.2% by weight, the liquid medium and the plurality of fibers may be agglomerated due to cohesive force, which leads to layering that hinders mixing.

In at least one embodiment of the present disclosure, when the amount of the plurality of fibers in the composition is about 0.25% by weight, the liquid medium can be added in a single step or multiple steps to form a liquid composition. For example, the prepared fiber, the freeze-dried tablet or dry powder comprising the plurality of fibers is mixed with water or another liquid medium to form a liquid composition, with the freeze-dried tablet or dry powder absorbing the liquid medium and disintegrated to form a liquid composition. In some embodiments of the present disclosure, a small amount of water or another liquid medium may be added first to make the plurality of fibers, freeze-dried tablet or dry powder form a thick liquid, and thereafter more water or liquid medium is added to further dilute the composition with better fluidity. For example, in some embodiments of the present disclosure, the amount of the plurality of fibers in the thick liquid formed in the first stage may be about 1.0% by weight, and after adding water or liquid medium one or more times, the content of the plurality of fibers may be between 0.1% by weight and 0.5% by weight. For example, it may be 0.1% by weight, 0.15% by weight, 0.2% by weight, 0.25% by weight, 0.3% by weight, 0.35% by weight, 0.4% by weight, 0.45% by weight or 0.5% by weight.

In at least one embodiment, the length-to-diameter ratio of the plurality of fibers prepared by the present disclosure may be between 60 and 150, e.g., 60, 65, 70, 75, 80, 85, 90, 95, 100, 105, 110, 115, 120, 125, 130, 135, 140, 141, 142, 143, 144, 145 or 150.

In at least one embodiment, the liquid composition formed by mixing the plurality of fibers and water prepared by the present disclosure may form a contact with the surface of the parafilm (Parafilm, Bemis, PM996) with an angle between about 950 to less than 110°, such as 95.5°, 96°, 96.5°, 97°, 97.5°, 98°, 98.5°, 99°, 99.5°, 100°, 100.5°, 101°, 101.5°, 102°, 102.5°, 103°, 103.5°, 104°, 104.5°, 105°, 105.5°, 106°, 106.5°, 107°, 107.5°, 108°, 108.5°, 1090 or 109.5°.

In at least one embodiment, the optical density value ($OD_{620}$) measured at a wavelength of 620 nanometers (nm) for a composition comprising the plurality of fibers at 0.2% to 1.2% by weight and 0.1 mL of water in the present disclosure is between 0.25 and 1.25. In some embodiments of the present disclosure, the lower limit of $OD_{620}$ may be 0.25, 0.26, 0.27, 0.28, 0.29, 0.3, 0.31, 0.33, 0.35, 0.37, 0.39, 0.4, 0.41, 0.43, 0.45, 0.5, 0.6, 0.7 or 0.8. In some embodiments of the present disclosure, the upper limit of $OD_{620}$ may be 1.25, 1.24, 1.23, 1.22, 1.21, 1.2, 1.1, 1, 0.9, 0.8, 0.7, 0.6 or 0.5. In some embodiments of the present disclosure, the value of the aforementioned $OD_{620}$ may be, for example, 0.295, 0.335, 0.435, 0.53, 0.54, 0.55, 0.65, 0.75, 0.76, 0.78, 0.85, 0.88, 0.93, 0.96, 0.98, 1.05, 1.08, 1.13, 1.14, 1.19, 1.215, or 1.225.

In at least one embodiment, the fibers of the present disclosure are obtained from biocellulose formed by one or more microorganisms through fiber separation procedures. The biocellulose can be formed from D-glucose linked with β(1→4) glycosidic bond to each other, therefore belonging to a β-1-4-glucan. In some embodiments of the present disclosure, biocellulose has higher purity unlike plant cellulose.

In at least one embodiment, the microorganisms disclosed in the present disclosure can be bacteria, and biocellulose can be produced by bacterial culture and fermentation. In some embodiments, the bacteria disclosed in the present disclosure may be at least one of the genus selected from the group consisting of *Gluconacetobacter, Acetobacter, Rhizobium, Sarcina, Pseudomonas, Achromobacter, Alcaligenes, Enterobacter, Azotobacter, Agrobacterium*, or any combination thereof. In some embodiments, the bacteria disclosed in the present disclosure may be at least one selected from the group consisting of *Acetobacter xylinum, Gluconacetobacter hansenii, Gluconacetobacter xylinus*, and *Gluconacetobacter sacchari*. In some embodiments of the present disclosure, *Gluconacetobacter xylinus* may be used to produce biocellulose, but it is not limited thereto. In some embodiments of the present disclosure, single bacterium or multiple bacteria can be used to produce biocellulose, and may be adjusted according to actual needs without limitation.

In order to provide the biocellulose for preparing the plurality of fibers of the present disclosure, a container containing a culture medium may first be allocated, and the aforementioned single bacterium or multiple bacteria may be cultured in the container containing the culture medium in a static manner for 24 to 96 hours (such as 24 hours, 36 hours, 48 hours, 60 hours, 72 hours, 84 hours, 96 hours). The absorbance (at a wavelength of 620 nm) of the bacterial concentration in the culture medium is controlled between 0.005 and 0.01, for example, about 0.005, about 0.006, about 0.007, about 0.008, about 0.009, or about 0.01. In some embodiments of the present disclosure, the pH value of the culture solution is controlled in an acidic environment, including between a pH of 0.5 and 6.5, for example, a pH of about 0.5, about 1.0, about 1.5, about 2.0, about 2.5, about 3.0, about 3.5, about 4.0, about 4.5, about 5.0, about 5.5, about 6.0 or about 6.5. In some embodiments of the present disclosure, the concentration of microorganisms in the culture medium is controlled in a range of between $10^2$ to $10^5$/mL, such as about $1\times10^2$/mL, about $5\times10^2$/mL, about $1\times10^3$/mL, about $5\times10^3$/mL, about $1\times10^4$/mL, about $5\times10^4$/mL or about $1\times10^5$/mL. In some embodiments of the present disclosure, the culture temperature may be controlled between 25° C. and 30° C., such as about 25° C., about 26° C., about 27° C., about 28° C., about 29° C., or about 30° C. In some embodiments of the present disclosure, the absorbance of the bacterial concentration in the culture medium, the pH value of the culture medium, the concentration of the microorganisms in the culture medium, the culture temperature or any combination thereof may be selected to control the culture of the microorganisms of the present disclosure.

As used herein, the term "static culture" refers to the formation of a fibrous membrane layer on the surface of the culture medium (i.e., the air-liquid interface) by bacteria in a non-woven manner. In addition, the container used for static culture can be a container with a wide and flat culture area, so as to regulate the oxygen consumption of bacteria with a lower container height, thereby modulating the diameter of the biocellulose formed. In some embodiments of the present disclosure, since the network structure formed by the biocellulose on the surface of the fiber membrane formed has a greater density and is more compact than the network structure inside the fiber membrane, the subsequent separation of interwoven biocellulose is facilitated by the static culture and culture conditions disclosed by the present disclosure.

As used herein, the term "fibrous membrane" refers to a layered object that is interwoven with a plurality of bio-fiber and has a multi-layer network structure. In some embodiments of the present disclosure, the thickness of the fibrous membrane may be between 20 μm and 30 μm, such as about 20 μm, about 22 μm, about 24 μm, about 25 μm, about 26 μm, about 28 μm or about 30 μm. In some embodiments of the present disclosure, the amount of biocellulose per unit area of the fibrous membrane is between 0.001 $g/cm^2$ and 0.002 $g/cm^2$, such as about 0.0011 $g/cm^2$, about 0.0012 $g/cm^2$, about 0.0013 $g/cm^2$, about 0.0015 $g/cm^2$, about 0.0017 $g/cm^2$, about 0.0018 $g/cm^2$, or about 0.0019 $g/cm^2$. In some embodiments of the present disclosure, the diameter of the biocellulose in the fibrous membrane is between 15 nm and 100 nm, such as about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm or 100 nm.

In at least one embodiment, the ingredients of the culture medium may include a carbon source, a nitrogen source, and a gel support, wherein the carbon source may include at least one sugar or sugar alcohol such as mannitol, glucose, molasses, etc., and the nitrogen source may include peptone, yeast extract or a combination thereof. The gel support may be selected from, for example, agar, and is not limited thereto. In some embodiments of the present disclosure, the culture medium may include agar, carbon source, peptone and yeast extract, wherein the weight ratio of the carbon source, peptone and yeast extract may be 5:1:1 to 4:1:1.

In at least one embodiment of the present disclosure, the fibrous membrane can be prepared by static fermentation of bacteria of the genus *Gluconobacter* in a culture medium comprising mannitol, peptone, yeast extract and agar, wherein the prepared fibrous membrane has a water content greater than 85%, such as greater than 90%, greater than 92% or greater than 95%.

In order to obtain fibers to be prepared for the prevention or treatment of gastroesophageal reflux disease, in at least one embodiment, the fibrous membrane is further subjected to a fiber separation procedure. The fiber separation procedure includes homogeneous pulverization of the fibrous membrane to obtain a dispersion, followed by swelling the interwoven biocellulose in the dispersion, and mechanical grinding of the swelled biocellulose.

As used herein, the term "homogeneous pulverization" refers to mixing a fibrous membrane with a solution, followed by use of a homogenizing device to pulverize with a fixed outer knife with shearing force and a saw-like and rotatable inner knife to prepare a dispersion.

In at least one embodiment of the present disclosure, after the dispersion is subjected to the aforementioned homogenous pulverization, other additives may be added to the dispersion to swell the interwoven biocellulose in the dispersion. The additives added in the present disclosure may include additives commonly used in the art, and are not limited thereto.

As used herein, the term "swelling" includes the penetration of the treatment liquid into the interwoven biocellulose in the dispersion to weaken the hydrogen bond between the cellulose, which does not lead to excessive hydrolysis of biocellulose and reduces the energy consumption in the subsequent mechanical grinding process. In some embodiments of the present disclosure, under the synergistic effect produced by the shearing force of the mechanical grinding, the glycosidic bonds of biocellulose are broken, thereby separating the biocellulose fibers. The specific surface area is thus increased with more exposed hydroxyl groups, thereby enhancing the hydrophilicity and biocompatibility of biocellulose.

In at least one embodiment, the treatment liquid of the present disclosure can be at least one selected from the group consisting of an alkali solution, an inorganic salt solution, and an ionic liquid aqueous solution. In some embodiments of the present disclosure, the base forming the alkaline solution includes at least one selected from the group consisting of potassium hydroxide, sodium hydroxide, and lithium hydroxide. In some embodiments of the present disclosure, the inorganic salt can be at least one selected from the group consisting of zinc chloride, thiourea, calcium chloride and magnesium chloride. In some embodiments of the present disclosure, the ionic liquid can be at least one selected from the group consisting of 1-allyl-3-methylimidazolium chloride ([AMIm]Cl), 1-butyl-3-methylimidazolium chloride ([BMIm]Cl), 1-allyl-3-methylimidazolium acetate ([AMIm]Ac), 1-butyl-3-methylimidazolium acetate [BMIm]Ac), lithium chloride/dimethyl sulfoxide (LiCl/DMSO), N-alkylpyridines and di-alkylimidazoles.

As used herein, the term "mechanical grinding" includes diluting the dispersion with water and grinding with a horizontal ball mill to separate the interwoven biocellulose fiber in the dispersion to form fibers with a diameter of 15 nm to 35 nm and a length of 1.5 m to 3.5 µm, wherein the amount of biocellulose used for mechanical grinding is between about 0.1% by weight and about 0.5% by weight of the total weight of the dispersion, such as about 0.15% by weight, about 0.2% by weight, about 0.25% by weight, about 0.3% by weight, about 0.35% by weight, about 0.4% by weight, or about 0.45% by weight. Thereafter, the swelled and mechanically ground dispersion is purified according to the conventional method, which includes neutralization and desalting, such as by dialysis using a semi-permeable membrane to separate the salts in the dispersion to obtain the desired fiber.

In at least one embodiment of the present disclosure, the ground biocellulose has a high specific surface area which enhances the electrostatic effect, Van der Waals force or hydrogen bonding between the cellulose, which may facilitate agglomeration. Therefore, in some embodiments, the present disclosure may include further processing the ground dispersion liquid by ultrasonication after mechanical grinding to de-agglomerate the agglomerates of biocellulose, which can be optionally subjected to freeze-drying according to actual needs.

In at least one embodiment, the composition of the present disclosure may include fibers formed of β-1-4-glucan and other substances, wherein the plurality of fibers may be presented in the form of freeze-dried tablets or dry powder and combined with other substances to form the composition. In some embodiments, the composition of the present disclosure may further include at least one selected from the group consisting of organic nutrients, probiotics, drugs, dietary fibers, flavoring agents, dispersants, wetting agents, lubricants, thickeners, stabilizers, preservatives, antioxidants, antibacterial agents, and coloring agents, while there is no negative influence of these substances on the plurality of fibers of the present disclosure. In some embodiments, the fibers of the present disclosure exhibit a synergetic effect with the above-mentioned substances.

In at least one embodiment, the organic nutrient of the present disclosure includes an extract extracted from a culture medium of the static culture of the microorganism above. In some embodiments of the present disclosure, the flavoring agent includes a sweetener and/or flavoring. In some embodiments of the present disclosure, the probiotics include, for example, *Enterococcus, Lactobacillus, Bacillus, Clostridium, Lactococcus lactis, Leuconostoc, Pediococcus, Carnobacterium, Vagococcus, Tetragenococcus, Bifidobacterium, Atopobium, Weissella, Abiotrophia, Granulicatella, Oenococcus, Paralactobacillus* and *Saccharomyces boulardii* and any combination thereof. In some embodiments of the present disclosure, the probiotics may be selected from *Lactobacillus acidophilus, Lactobacillus casei, Lactobacillus reuteri, Bifidobacterium bifidum, Bifidobacterium lactis, Lactobacillus johnsonii, Lactobacillus paracasei, Lactobacillus rhamnosus, Bifidobacterium longum* and any combination thereof.

In at least one embodiment, the drug disclosed in the present disclosure may be a western medicine or a Chinese medicine, for example, a Chinese medicine or a western medicine clinically used for gastroesophageal reflux disease or a Chinese medicine or a western medicine that has the potential to be used as a medicine for the treatment of gastrointestinal diseases. For example, the traditional Chinese medicine can be *Bletilla striata, Notoginseng Radix et Rhizoma, Cyperi Rhizoma, Corydalis Rhizoma, Curcumae Radix, Toosendan Fructus, Massa Medicata Fermetata, Hordei Fructus Germinatus, Galli Gigerii Endothelium Coreneum, Raphani Semen, Codonopsis Radix, Atractylodis Macrocephalae Rhizoma, Poria, Dioscoreae Rhizom, Bupleuri Radix*, White Peony Rot *Aurantii Fructus, Amomi Fructus*, liquorice, *Endoconcha Sepiae*, Fritillary, Bergamot, *Atractylodes lancea, Magnolia officinalis, Scrophulariae Radix, Adenophora stricta, Rehmanniae Radix, Angelicae Sinensis Radix, Rhei Radix et Rhizoma, Coptidis Rhizoma, Scutellariae Radix, Hematite, Perillae Fructus, Inulae Flos, Rehmanniae Radix, Astragali Radix, Aucklandiae Radix, Leonuri Herba, Coicis Semen, Pinelliae Rhizoma, Bambusae Caulis* in *Taenias, Gardeniae Fructus, Zingiberis Rhizoma Recens, Fritillariae Thunbergii Bulbus, Agastache Rugosa, Puerariae Lobatae Radix, Platycodonis Radix, Forsythiae Fructus, Menthae Haplocalycis Herba, Lasiosphaera Calvatia, Picrorhizae Rhizoma, Persicae Semen, Carthami Flos, Crataegi Fructus, Ulmus macrocarpa* Hance, *Pinelliae* decoction for purging stomach fire, *Bupleurum* & *Rehmannia* Combination, *Evodia* decoction, *Citrus* & Cratagus Formula, Major Four Herb Combination, Major Six Herb Combination, Saussures & *Cardamon* Combination, *Ophiopogon* Combination, *Bupleurum* & *Cyperus* Combination, *Coptis* & Rhubarb Combination, An Zhong San Extract Granules, Left Metal Pill, *Pinelliae* and *Magnoliae officinalis* decoction, Forsythia & Rhubarb Formula, Tangerine peel and bamboo shavings decoction, Cloves and kaki calyx decoction, *Bupleurum* & Chih Shih Formula, Minor *Pinellia* decoction, *Magnolia* & Ginger Formula, Effective Integration Decoction, Stomach-Boosting Decoction, Wu Pei San, *Bupleurum* & Peony Formula, Hoelen & Bamboo Combination with *Coptidis*, Drink of Salviae Miltiorrhizae Radix et Rhizoma, Forsythia & Rhubarb Formula and any combination thereof.

In some embodiments of the present disclosure, the plurality of fibers formed of β-1-4-glucan or a composition comprising the same can be administered when the symptoms are predicted to occur or before the symptoms occur, in order to achieve the effect of prevention and protection. For example, the composition in a form of freeze-dried tablet of the present disclosure can be administered to the subject in need of prevention or treatment of gastroesophageal reflux disease at a dose for 1 to 4 times a day, and each dose of freeze-dried tablet administered comprises 0.02 g to 0.12 g of the plurality of fibers. In some embodiments of the present disclosure, when the plurality of fibers formed of β-1-4-glucan is directly administered, it is administered 1 to 4 times a day to a subject in need of prevention or treatment of gastroesophageal reflux disease, and each administration comprises 0.02 grams to 0.12 grams of fibers.

In some embodiments of the present disclosure, the plurality of fibers formed of β-1-4-glucan or the composition comprising the same can be administered at the time or after the occurrence of the symptoms to relieve the symptoms. In some embodiments of the present disclosure, the route and form of administration are described above.

In at least one embodiment of the present disclosure, the plurality of fibers formed of β-1-4-glucan or a composition comprising the same can be taken orally twice a day to treat or relieve the aforementioned symptoms with an interval of 1 to 12 hours; for example, the interval can be 1 hour, 2 hours, 3 hours, 4 hours, 5 hours, 6 hours, 7 hours, 8 hours, 9 hours, 10 hours, 11 hours or 12 hours. In some embodiments of the present disclosure, the plurality of fibers formed of β-1-4-glucan or the composition comprising the same can be administered before a meal, after a meal, or before going to bed. In at least one embodiment, the plurality of fibers formed of β-1-4-glucan or the composition comprising the same can be orally administered three times a day at an interval of 4 to 8 hours. Optionally, the plurality of fibers or the composition may be administered more than 3 times a day, e.g., 4 times, until a more obvious relief symptom has been obtained.

The present disclosure is further explained in more detail by reference to the following embodiments; however, the embodiments are not intended to limit the scope of the present disclosure.

EMBODIMENTS

Evaluation and Diagnosis of Gastroesophageal Reflux Disease

Gastroesophageal reflux disease is diagnosed by a physician with an esophagogastroduodenoscopy (gastroscope), a 24-hour esophageal pH test, an esophageal impedance pH study, a lower esophageal sphincter pressure test, a barium swallow radiograph, a proton pump inhibitor test, consultation and patient self-assessment questionnaire. The following examples are conducted on recruited patients diagnosed with gastroesophageal reflux disease.

Evaluation of Effects of Fibers Formed of β-1-4-Glucan in Relieving Symptoms of Gastroesophageal Reflux Disease After a trial, a 7-point balanced scale was used by patients to answer the following questions: "Compared to the condition before entering the trial, how do you evaluate the relief of your symptoms of gastroesophageal reflux disease, including typical symptoms such as heartburn, acid reflux; atypical symptoms such as non-cardiac chest pain, dysphagia, foreign body sensation in the throat, nausea, persistent cough, wheezing, hoarse throat, sore throat etc.?" Effect of fibers formed of β-1-4-glucan was evaluated based on the patient's response to symptom relief.

7-point balance scale:
  Significant relief
  Moderate relief
  Slight relief
  Unchanged
  Slightly severe
  Moderately severe
  Significantly severe Among these, those who answered significant relief, moderate relief, and slight relief were considered as effective.

Example 1

Trial Method

Patients are allowed to take a dose of composition orally before lunch and dinner every day, where the composition comprises 0.2% by weight of fibers formed of β-1-4-glucan with the balance being water as one dose.

Subject 1

A 60-year-old female patient with gastroesophageal reflux complained of symptoms occurring 1 to 2 times a week. The composition comprising fibers formed of β-1-4-glucan was taken every day according to the trial method above, and the trial duration was up to 4.5 months. The patient answered the above questions on a 7-point balance scale, and the results showed that the composition was effective and there was no more discomfort due to gastroesophageal reflux after taking the composition. No adverse reaction and side effect was reported by the patient.

Subject 2

A 42-year-old female patient of gastroesophageal reflux complained of symptoms occurring 1 to 2 times a week. The composition comprising fibers formed of β-1-4-glucan was taken every day according to the trial method above, and the trial duration was up to 2 months. The patient answered the above questions on a 7-point balance scale, and the results showed that the composition was effective and there was no more discomfort due to gastroesophageal reflux after taking the composition. No adverse reaction and side effect was reported by the patient.

Example 2

Trial Method

Patients are to take a dose of the composition orally at the time of symptom onset, where the composition comprises 0.2% by weight of fibers formed of β-1-4-glucan with the balance being water as one dose.

Subject 1

A 59-year-old male patient diagnosed of gastroesophageal reflux disease took the composition comprising fibers formed of β-1-4-glucan according to the trial method above, and the trial duration lasted for half a year. The patient answered the above questions on a 7-point balance scale, and the results showed that the composition was effective. No adverse reaction and side effect was reported by the patient.

Subject 2

A 42-year-old female patient diagnosed of gastroesophageal reflux disease took the composition comprising fibers formed of β-1-4-glucan according to the trial method above, and the trial duration lasted for 4 months. The patient answered the above questions on a 7-point balance scale, and the results showed that the composition was effective. No adverse reaction and side effect was reported by the patient.

Subject 3

A 59-year-old female patient with gastroesophageal reflux complained of frequent chest burning and discomfort of acid reflux. The patient took the composition comprising fibers formed of β-1-4-glucan according to the trial method above, and the trial duration lasted for 3 months. The patient answered the above questions on a 7-point balance scale, and the results showed that the composition was effective. No adverse reaction and side effect was reported by the patient.

Subject 4

A 26-year-old male patient with gastroesophageal reflux complained of weekly occurring classical symptoms of gastroesophageal reflux disease including heartburn and nausea. The patient took the composition when the symptoms occur for a month, where the composition was taken whenever the symptoms occurred. The patient answered the above questions on a 7-point balance scale, and the results showed that the composition was effective. No adverse reaction and side effect was reported by the patient.

Subject 5

A 38-year-old male patient with gastroesophageal reflux complained of frequent occurring symptoms of gastroesophageal reflux disease for at least 1 to 3 times a week. In the beginning of the trial, the patient took 1 or 2 doses of the composition above for 1 week, where the composition was taken whenever the symptoms occurred. The patient answered the above questions on a 7-point balance scale, and the results showed that the composition was effective. The patient reported that the symptoms were relieved 5 minutes after taking the composition with an excellent effect.

After the above trial, the patient was switched to an additional trial by taking 2 oral doses of the composition taken by Subject 1 above every day (choosing any 2 timings before lunch, before dinner or before bed) for 3 weeks. After the trial, the patient answered the above questions on a 7-point balance scale, and the results showed that the composition was effective. The patient reported that the symptoms of gastroesophageal reflux disease occurred only once during the trial period of 3 weeks, and no symptoms of gastroesophageal reflux disease occurred in a month after the end of the trial.

Subject 6

A 41-year-old female patient with gastroesophageal reflux complained of frequent occurring symptoms of gastroesophageal reflux disease for at least 1 to 2 times a week. The patient took the antacids prescribed by a doctor regularly and the symptoms discontinued. However, the symptoms recurred after the antacids were stopped. The patient entered the trial of the present disclosure and stopped taking antacids, and instead the patient took a dose of the composition above whenever the symptoms occurred. The patient answered the above questions on a 7-point balance scale, and the results showed that the composition was effective. The patient reported that the symptoms were relieved 5 to 10 minutes after taking the composition, which can be used to replace antacids.

What is claimed is:

1. A method for preventing or treating gastroesophageal reflux disease, comprising administering to a subject in need thereof a plurality of fibers formed of β-1-4-glucan and a carrier thereof,
   wherein the fibers the fibers are formed by fermentation of at least one bacterium selected from the group consisting of *Gluconacetobacter, Acetobacter, Rhizobium, Sarcina, Pseudomonas, Achromobacter, Alcaligenes, Enterobacter, Azotobacter* and *Agrobacterium*,
   wherein the fibers have a diameter of between 15 nm and 35 nm and a mean length of between 1.5 μm and 3.5 μm,
   wherein the fibers are administered orally to the subject at an effective amount for 1 to 4 times a day, wherein every dose administered includes 0.02 g to 0.12 g of the plurality of fibers, and
   wherein the gastroesophageal reflux disease is grade A or grade B erosive esophagitis graded by Los Angeles classification.

2. The method of claim 1, wherein the fibers have a length-to-diameter ratio of from 60 to 150.

3. The method of claim 1, wherein the fibers are comprised in a composition and administered to the subject in need of prevention or treatment of gastroesophageal reflux disease.

4. The method of claim 3, wherein the composition is in a form of a freeze-dried tablet.

5. The method of claim 3, wherein the composition is administered to the subject in a form comprising the plurality of fibers formed of β-1-4-glucan and a liquid medium.

6. The method of claim 5, wherein the liquid medium is water.

7. The method of claim 5, wherein the fibers are in an amount of from 0.2% by weight to 1.2% by weight based on a total weight of the composition.

8. The method of claim 7, wherein the composition comprises 0.1 mL of water with $OD_{620}$ between 0.25 and 1.25.

9. The method of claim 8, wherein the $OD_{620}$ is between 0.4 and 1.22.

10. The method of claim 1, wherein the bacterium is at least one selected from the group consisting of *Gluconacetobacter hansenii, Gluconacetobacter xylinus*, and *Gluconacetobacter sacchari*.

11. The method of claim 3, wherein the composition further includes at least one selected from the group consisting of an organic nutrient, a probiotic, a drug, a dietary fiber, a flavoring agent, a dispersing agent, a wetting agent, a lubricant, a thickening agent, a stabilizer, a preservative, an antioxidant, an antibacterial agent and a coloring agent.

* * * * *